United States Patent
Gibson et al.

(10) Patent No.: US 6,440,493 B1
(45) Date of Patent: *Aug. 27, 2002

(54) EMULSION-BASED PROCESSES FOR MAKING MICROPARTICLES

(75) Inventors: John W. Gibson, Springville, AL (US); Richard J. Holl, Ft. Collins, CO (US); Arthur J. Tipton, Birmingham, AL (US)

(73) Assignee: Southern Biosystems, Inc., Birmingham, AL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/726,108

(22) Filed: Nov. 29, 2000

Related U.S. Application Data

(63) Continuation-in-part of application No. 09/303,842, filed on May 3, 1999, now Pat. No. 6,291,013, and a continuation-in-part of application No. PCT/US00/11781, filed on May 2, 2000.

(51) Int. Cl.$^7$ .............................. A61K 9/16; B01J 13/12

(52) U.S. Cl. .............................. 427/213.3; 427/213.31; 427/213.32; 427/213.33; 427/213.36; 428/402.2; 428/402.21; 264/4.1; 264/4.3; 264/4.33; 264/4.6

(58) Field of Search .......................... 427/213.3, 213.31, 427/213.32, 213.33, 213.36; 428/402.2, 402.21; 264/4.1, 4.3, 4.33, 4.6

(56) References Cited

U.S. PATENT DOCUMENTS

| | | |
|---|---|---|
| 3,891,570 A | 6/1975 | Fukushima et al. |
| 4,299,501 A | 11/1981 | Patil et al. |
| 4,384,975 A | 5/1983 | Fong |
| 4,389,330 A | 6/1983 | Tice et al. |
| 4,469,648 A | 9/1984 | Ferraris et al. |
| 4,530,840 A | 7/1985 | Tice et al. |
| 4,818,542 A | 4/1989 | DeLuca et al. |
| 5,407,609 A | 4/1995 | Tice et al. |
| 5,478,564 A | 12/1995 | Wantier et al. |

(List continued on next page.)

FOREIGN PATENT DOCUMENTS

| | | |
|---|---|---|
| CH | 653 553 A5 | 1/1986 |
| EP | 0 102 265 B1 | 7/1983 |
| EP | 0 779 072 A1 | 6/1997 |
| GB | 2 310 801 A | 9/1997 |
| WO | WO 93/17668 A1 | 9/1993 |
| WO | WO 97/41837 A2 | 11/1997 |
| WO | WO 98/35654 A1 | 8/1998 |
| WO | WO 98/46212 A1 | 10/1998 |
| WO | WO 00/40221 A1 | 7/2000 |

OTHER PUBLICATIONS

Benita, ed., *Microencapsulation: Methods and Industrial Applications* (Marcel Dekker, Inc., New York 1996).
Burns, et al., "Control of estrus and ovulation in mares using progesterone and estradiol biodegradable microspheres in a multicenter clinical trial," Proceed. Intern. Symp. Control. Mater. 21:114–15 (1994).
Burns, et al., "Evaluation of a new continuos process for preparation of progesterone and estradiol microspheres: an In–Vivio pharmokinetics study," CRS Abstract #7603 (1996).
Burns, et al., "Evaluation of biodegradable microsphere for the controlled release of progesterone and estradiol in an ovulation control program for cycling mares," Journal of Equine Veterinary Science 13:521–524 (1993).
Choi, et al., "Block copolymer nanoparticles of ethylene oxide and isobutyl cyanoacrylate," Macromolecules 28:8419–8421 (1995).
Donbrow, ed., *Microcapsules and Nanoparticles in Medicine and Pharmacy* (CRC Press, Boca Raton, 1992).
Li, et al., "Kinetic and thermodynamic modeling of the formation of polymeric microspheres using solvent extraction/evaporation method," Journal of Controlled Release 37:187–198 (1995).
Li, et al., "Prediction of solvent removal profile and effect on properties for peptide–loaded PLGA microspheres prepared by solvent extraction/evaporation method," Journal of Controlled Release 37:199–214 (1995).
Maa, et al., "Liquid–liquid emulsification by static mixers for use in microencapsulation," J. Microencapsulation 13(4):419–33 (1996).
Shiga, et al., "Preparation of poly (D,L–lactide) and copoly-(lactide–glycolide) microspheres of uniform size," J. Pharm. Pharmacol 48:891–895 (1996).

Primary Examiner—Nathan M. Nutter
(74) Attorney, Agent, or Firm—Holland & Knight LLP

(57) ABSTRACT

Processes for making microparticles, preferably containing an active agent, are provided. In a preferred embodiment, the process involves preparing (1) a dispersed phase containing an agent in a solution of polymer and a first solvent; (2) a continuous phase containing a surfactant, and a second solvent that is totally or partially immiscible with the first solvent; and (3) an extraction phase that is a nonsolvent for the polymer, a solvent for the continuous phase components, and a solvent for the first solvent, wherein the first solvent has solubility in the extraction phase of between about 0.1% and 25% by weight. Then, the dispersed phase and the continuous phase are mixed to form an emulsion, and the emulsion is then briefly mixed with a suitable quantity of extraction phase to induce skin formation at the interface of the dispersed and continuous phases. Remaining solvent is removed by an evaporation process step. The emulsification and solvent removal steps are preferably conducted in a continuous process. The brief extraction step prior to evaporation minimizes the loss of active agent from the microparticles, and reduces the required volume of extraction phase as compared to other extraction-based processes. Alternate emulsification methods and solvent removal methods, such as incremental extraction, cryogenic extraction, or membrane separation, also are provided, and can be used in various combinations to make microparticles.

36 Claims, 4 Drawing Sheets

U.S. PATENT DOCUMENTS

| | | |
|---|---|---|
| 5,635,216 A | 6/1997 | Thompson |
| 5,643,605 A | 7/1997 | Cleland et al. |
| 5,650,173 A | 7/1997 | Ramstack et al. |
| 5,654,008 A | 8/1997 | Herbert et al. |
| 5,705,197 A | 1/1998 | Van Hamont et al. |
| 5,718,921 A | 2/1998 | Mathiowitz et al. |
| 5,792,477 A | 8/1998 | Rickey et al. |
| 5,817,343 A | 10/1998 | Burke |
| 5,912,017 A | 6/1999 | Mathiowitz et al. |
| 5,916,598 A | 6/1999 | Rickey et al. |
| 5,922,253 A | 7/1999 | Herbert et al. |
| 6,291,013 B1 * | 9/2001 | Gibson et al. ............ 427/213.3 |

* cited by examiner

EMULSION-BASED PROCESSES FOR MAKING MICROPARTICLES

CROSS-REFERENCE TO RELATED APPLICATIONS

This is a continuation-in-part of both U.S. application Ser. No. 09/303,842, filed May 3, 1999, and now U.S. Pat. No. 6,281,013 and international application PCT/US00/11781, filed May 2, 2000.

BACKGROUND OF THE INVENTION

The present invention generally relates to methods of preparing microparticles, and more particularly to methods of preparing microparticles encapsulating biologically active agents, such as therapeutic agents.

Several methods for preparing microparticles are well known in the art. Examples of these processes include single and double emulsion solvent evaporation, spray drying, solvent extraction, phase separation, simple and complex coacervation, and interfacial polymerization. Methods developed for making microparticles for drug delivery are described in the literature, for example, in Doubrow, ed., "Microcapsules and Nanoparticles in Medicine and Pharmacy" (CRC Press, Boca Raton 1992) and Benita, ed., "Microencapsulation: Methods and Industrial Applications" (Marcel Dekker, Inc., New York 1996).

Emulsion-based processes usually begin with the preparation of two separate phases: a first phase, which generally consists of a dispersion or solution of an active agent in a solution of polymer dissolved in a first solvent, and a second phase, which generally consists of a solution of surfactant and a second solvent that is at least partially immiscible with the first solvent of the dispersed phase. After the first and second phases are prepared, they are combined using dynamic or static mixing to form an emulsion, in which microdroplets of the first phase are dispersed in the second, or continuous, phase. The microdroplets then are hardened to form polymeric microparticles that contain the active agent. The hardening step is carried out by removal of the first solvent from the microdroplets, generally by either an extraction or evaporation process.

Several U.S. patents describe solvent removal by extraction. For example, U.S. Pat. No. 5,643,605 to Cleland et al. discloses an encapsulation process in which the emulsion is transferred to a hardening bath (i.e. extraction medium) and gently mixed for about 1 to 24 hours to extract the polymer solvent. The long period of time required for extraction is undesirable, particularly if the process is to be operated continuously. Others have disclosed processes that compensate for the unfavorable thermodynamics (slow and incomplete extraction) by using a large excess of extraction medium. For example, U.S. Pat. No. 5,407,609 to Tice et al. teaches transferring the emulsion to a volume of extraction medium that is preferably ten or more times the volume required to dissolve all of the solvent in the microdroplets, so that greater than 20–30% of the solvent is immediately removed. U.S. Pat. No. 5,654,008 to Herbert et al. similarly discloses a process in which the volume of quench liquid, or extraction medium, should be on the order of ten times the saturated volume. The use of a large excess of extraction medium rapidly extracts a portion of the solvent from each microdroplet, creating a concentration gradient within each droplet and forming a polymer skin on the surface that advantageously traps active agent, but which disadvantageously slows extraction of the remaining solvent from the center portion of the microdroplet. Larger volumes of extraction medium also may increase process equipment and operating costs, as well as the costs associated with recycling or disposing of used extraction medium.

Evaporation is another approach known in the art for solvent removal. For example, U.S. Pat. No. 3,891,570 to Fukushima et al. and U.S. Pat. No. 4,384,975 to Fong teach solvent removal by evaporating an organic solvent from an emulsion, preferably under reduced pressure or vacuum. Solvent evaporation processes generally occur slowly enough such that the solvent/polymer composition remains uniform throughout each microdroplet during the evaporation step, such that a polymer skin is not created. For this same reason, however, the evaporation process is not favored for use with many active agents that partition into the continuous phase, resulting in significant loss of active agent into the continuous phase and/or the extraction medium, and consequently poor loading of active agent in the microparticle. Evaporation, however, would be highly desirable if such partitioning could be substantially avoided, since no extraction phase solvent and associated tanking and piping are required as in the extraction process.

One effort combining evaporation and extraction is disclosed in U.S. Pat. No. 4,389,330 to Tice et al. ("Tice '330"). Tice '330 describes an emulsion-based method for making drug-loaded polymeric microspheres that uses a two-step solvent removal process: evaporation followed by extraction. The evaporation step is disclosed to be conducted by application of heat, reduced pressure, or a combination of both, and is purported to remove between 10 and 90% of the solvent. Tice '330 also discloses that the extraction medium with dissolved solvent must be removed and replaced with fresh extraction medium, preferably on a continual basis. Consequently, the process requires either large volumes of extraction medium or an intermediate isolation of the microspheres combined with a change in the composition of the extraction medium.

Li et al., *J. Controlled Release* 37:188–214 (1995) ("Li et al.") describes a model of a solvent removal process in which an emulsion of the dispersed phase is formed in a continuous phase devoid of dispersed phase solvent, extracting a portion of the dispersed phase solvent into the original volume for a brief period of time, and then further extracting the dispersed phase solvent by diluting the emulsion by continuous addition of continuous phase solvent. Evaporation of the dispersed phase solvent from the continuous phase/air interface is allowed to occur simultaneously with the extraction process, to maintain a driving force for extraction of the dispersed phase solvent into the continuous phase from the dispersed phase droplets. Uncontrolled evaporation of solvent from the open extraction vessel into the atmosphere is not practical or safe for production of greater than laboratory scale quantities, especially in a continuous process. In a closed vessel, the evaporation would rapidly cease as the solvent in solution equilibrated with the solvent vapor in the head space above the liquid surface. The Li et al. model also demonstrates that large extraction volumes are needed to operate the extraction process in relatively short time periods, as described in U.S. Pat. No. 5,407,609 to Tice et al., although the model predicts that skin formation and the glassy boundary can be achieved using total extraction solvent volumes that are less than the amount needed to dissolve all of the dispersed phase solvent.

It is therefore an object of this invention to provide methods for making microparticles efficiently encapsulating active agent.

It is another object of this invention to provide methods for making microparticles using a process that uses evaporation, controlled extraction, or a combination thereof to minimize the amount of extraction medium required in the process.

It is a further object of this invention to provide alternative methods of emulsion formation and solvent removal for use in processes of making microparticles.

It is another object of this invention to provide emulsion-based methods for making microparticles in an efficient batch or continuous process.

SUMMARY OF THE INVENTION

Processes for making polymeric microparticles, preferably including one or more active agents, have been developed. In a preferred embodiment, the process involves preparing (1) a dispersed phase containing an agent in a solution of polymer and a first solvent; (2) a continuous phase containing a surfactant, and a second solvent that is totally or partially immiscible with the first solvent; and (3) an extraction phase that is a nonsolvent for the polymer, a solvent for the continuous phase components, and a solvent for the first solvent, wherein the first solvent (or the first solvent component of greatest proportion if a mixture of solvents are used for the first solvent) has solubility in the extraction phase of between about 0.1% and 25% by weight. This limited solubility of the first solvent is important to maintain the stability of the emulsion as it is diluted. An emulsion of the dispersed phase in the continuous phase is prepared under appropriate mixing conditions, and the emulsion is then briefly mixed with a suitable quantity of extraction phase to concentrate the dispersed phase to induce skin formation at the interface of the dispersed and continuous phases. Remaining solvent is removed by an evaporation process step. The emulsification and solvent removal steps are preferably conducted in a continuous process. The brief extraction step prior to evaporation minimizes the loss of active agent from the microparticles, and reduces the required volume of extraction phase as compared to other extraction-based processes.

Alternate solvent removal processes are also provided. Some of these processes can be utilized in place of, or in combination with, known solvent removal processes and the preferred embodiment described above. In another preferred embodiment, solvent is removed using incremental, or cascade, extraction which involves introducing the extraction phase into the emulsion through a (temporal, not spatial) series of feed streams rather than a single feed stream, in order to slow and finely control the extraction of the solvent. In a further embodiment, solvent is removed by membrane separation, rather than direct mixing with the extraction phase. Other embodiments use cryogenic extraction, and two-phase solvent extraction, in which a single phase is used as the continuous phase and the extraction medium.

In preferred embodiments, the prepared continuous phase further includes dispersed phase solvent (i.e. first solvent), typically between about 10% and 100% of the amount needed to saturate the continuous phase.

In another preferred embodiment, a continuous process for making microparticles is provided, wherein the solvent is removed by evaporation, without the need for an extraction phase.

Alternate means of and processes for emulsion formation also are provided. For example, an emulsion lag tube, which is a small diameter tube of sufficiently high Reynolds number, is used to induce mixing in one embodiment of the process for making microparticles, rather than using conventional static mixers or agitators.

DETAILED DESCRIPTION OF THE INVENTION

Figure 1:
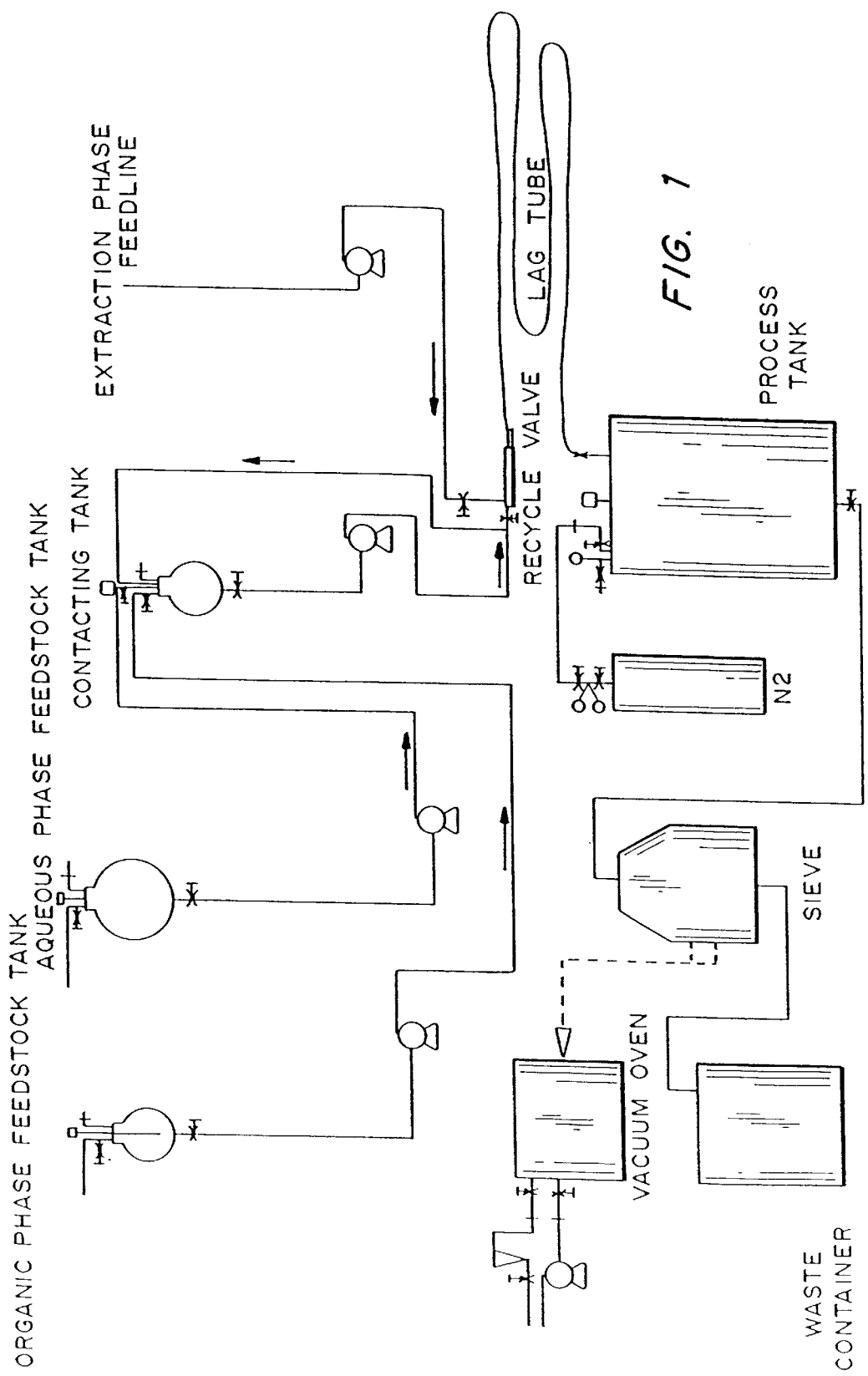
FIG. 1 is a process flow diagram of another embodiment of the method for making microparticles using a contacting tank with recycle, in a continuous process.

Emulsion-based processes for making microparticles are provided. A microparticle, as defined herein, comprises a particle having a diameter of less than about one millimeter. A microparticle can have a spherical, non-spherical, or irregular shape. The preferred microparticle shape is spherical, having a diameter between about 0.1 and 1000 μm. The terms "microparticle" and "microsphere" as used herein are interchangeable unless otherwise indicated.

I. Process Materials

A. Excipient

The processes disclosed herein can be used to form microparticles from a variety of materials, preferably biocompatible and biodegradable polymers. Biodegradable, as defined herein, means the polymer will degrade or erode in vivo to form smaller chemical species, wherein the degradation can result, for example, from enzymatic, chemical, and physical processes. The term "biocompatible" is used herein to refer to a polymer and any degradation products of the polymer that are non-toxic to a recipient and present no significant, deleterious or untoward effects on the recipient's body. Examples of suitable biocompatible, biodegradable polymers include polyhydroxy acids, such as poly(lactide)s, poly(glycolide)s, poly(lactide-co-glycolide)s, poly(lactic acid)s, poly(glycolic acid)s, and poly(lactic acid-co-glycolic acid)s. polyanhydrides, polyorthoesters, polyetheresters, polycaprolactone, polyesteramides, polyphosphazines, polycarbonates, polyamides, and copolymers and blends thereof. Biocompatible, non-biodegradable polymers suitable for use in the processes described herein include polyacrylates, ethylene-vinyl acetate copolymers, modified celluloses such as cellulose ethers and cellulose esters, non-degradable polyurethanes, polystyrenes, polyvinyl chloride, polyvinyl fluoride, poly(vinyl alcohol), poly(vinyl imidazole), chlorosulphonate polyolefins, polyethylene oxide, and copolymers and blends thereof.

Representative natural excipient materials include polysaccharides and proteins.

Poly(lactide)s, poly(glycolide)s, poly(lactide-co-glycolide)s, poly(lactic acid)s, poly(glycolic acid)s, poly (lactic acid-co-glycolic acid)s, polyanhydrides, polyorthoesters, polyetheresters, polycaprolactone, polyesteramides, cellulose ethers, cellulose esters, and acrylics are preferred polymers. Poly(DL-lactide-co-glycolide) ("PLG") is especially preferred.

B. Dispersed Phase Solvent

The selection of the dispersed phase solvent used in the process generally depends on the polymer and active agent chosen, as well as the particular means of solvent removal to be employed. Organic solvents, such as acetone, methyl ethyl ketone, ethyl lactate, ethyl acetate, dichloromethane, and ethyl acetate/alcohol blends, are preferred for use with PLGs, cellulose ethers, cellulose esters, and acrylics. For other polymers, such as polyethylene glycol, poly(vinyl alcohol), and carboxymethylcellulose, water may be preferred.

The amount of the dispersed phase solvent used in the process should be selected to provide a dispersed phase viscosity suitable for forming an emulsion using the selected mixing means described below. The viscosity generally should be less than about 5000 cP, and preferably is less than about 100 cP, more preferably less than about 10 cP.

C. Continuous Phase

Generally, the solvent for the continuous phase is aqueous when the dispersed phase is organic, and the continuous phase is non-aqueous when the dispersed phase is aqueous. The continuous, or second, phase preferably is aqueous and contains at least one surfactant or emulsifying agent. Polyvinyl alcohol is a preferred surfactant when water is used as the continuous phase solvent. Other emulsifiers or surfactants which may be used include most physiologically acceptable emulsifiers, for instance egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline. Emulsifiers also include surfactants such as free fatty acids, esters of fatty acids with polyoxyalkylene compounds like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and co-polymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di-, and tri-glycerides of saturated or unsaturated fatty acids, glycerides or soya-oil and sucrose. Other emulsifiers include natural and synthetic forms of bile salts or bile acids, both conjugated with amino acids and unconjugated such as taurodeoxycholate, and cholic acid.

The surfactant should be present in a concentration sufficient to form a stable emulsion with the dispersed phase using the mixing means selected. For example, if the process relies on low-intensity emulsification, such as emulsion lag tube turbulence (described below), then enough surfactant must be present to lower the surface tension of the continuous phase. Preferably, the surfactant should constitute between about 0.1 and 20% by weight of the continuous phase.

The continuous phase also preferably includes dispersed phase solvent, which reduces or eliminates partitioning of the solvent from the dispersed phase into the continuous phase during emulsification. The amount of dispersed phase solvent added to the continuous phase may vary depending on the specific excipient/active agent combination used. Generally, the amount of dispersed phase solvent is between about 10% and 100% of the amount needed to saturate the continuous phase.

D. Extraction Phase

The extraction phase, also called the extraction medium, is chosen to be a solvent for the continuous phase components, a limited solvent for the dispersed phase solvent, and a nonsolvent for the excipient. The first solvent (or the first solvent component of greatest proportion if a mixture of solvents are used for the first solvent) should have a solubility in the extraction phase of between about 0.1% and 25% by weight. When water insoluble excipients are used, the extraction phase preferably is deionized water. The extraction phase can contain buffers to limit active agent solubility in the extraction phase.

Any of the common buffers, such as phosphate, acetate, or tris, are suitable, provided that they are compatible with the surfactant system chosen. When making microparticles for pharmaceutical or biomedical applications, the buffer also should be pharmaceutically acceptable. The buffering system should be selected to provide a pH in the extraction phase which provides minimum solubility of the active agent.

Other suitable extraction phases can be used depending on the specific excipient/drug/surfactant system being used. For example, water-soluble organic solvents that are nonsolvents for the excipient can be used as a component of the extraction phase to increase the capacity of the extraction phase to extract the dispersed phase solvent. Examples that are useful for PLGs include alcohols, particularly poly (hydric alcohols) such as glycerol. When water is used as the dispersed phase solvent, extraction phase solvents such as a ethyl acetate, long chain alcohols and ketones (C5–C10) may be used alone or in combination as the extraction phase. When using the cryogenic extraction process described below, the extraction phase preferably is glycerol.

E. Active Agent

Essentially any substance, or agent, can be encapsulated using the processes described herein. The substance preferably is an active agent. As used herein, the term "active agent" refers to an agent which possesses therapeutic, prophylactic, or diagnostic properties in vivo, for example when administered to an animal, including mammals, such as humans. The term "active agent" also includes other (non-active) substances to be encapsulated, unless otherwise indicated. Examples of suitable therapeutic and/or prophylactic active agents include proteins, such as hormones, antigens, and growth factors; nucleic acids, such as antisense molecules; and smaller molecules, such as antibiotics, steroids, decongestants, neuroactive agents, anesthetics, and sedatives. Examples of suitable diagnostic and/or therapeutic active agents include radioactive isotopes and radioopaque agents.

The active agent can include organic molecules such as a drug, peptide, protein, carbohydrate (including monosaccharides, oligosaccharides, and polysaccharides), nucleoprotein, mucoprotein, lipoprotein, synthetic polypeptide or protein, or a small molecule linked to a protein, glycoprotein, steroid, nucleic acid (any form of DNA, including cDNA, or RNA, or a fragment thereof), nucleotide, nucleoside, oligonucleotides (including antisense oligonucleotides), gene, lipid, hormone, vitamin, including vitamin C and vitamin E, or combination thereof.

Representative therapeutic active agents include immunosuppressants, antioxidants, anesthetics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, antipsychotics, and radiation absorbers, including UV-absorbers. Other non-limiting examples of active agents include anti-infectives such as nitrofurazone, sodium propionate, antibiotics, including penicillin, tetracycline, oxytetracycline, chlorotetracycline, bacitracin, nystatin, streptomycin, neomycin, polymyxin, gramicidin, chloramphenicol, erythromycin, and azithromycin; sulfonamides, including sulfacetamide, sulfamethizole, sulfamethazine, sulfadiazine, sulfamerazine, and sulfisoxazole, and anti-virals including idoxuridine; anti-allergenics such as antazoline, methapyritene, chlorpheniramine, pyrilamine prophenpyridamine, hydrocortisone, cortisone, hydrocortisone acetate, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; decongestants such as phenylephrine, naphazoline, and tetrahydrazoline; miotics and anticholinesterases such as pilocarpine, esperine salicylate, carbachol, diisopropyl fluorophosphate, phospholine iodide, and demecarium bromide; parasympatholytics such as atropine sulfate, cyclopentolate, homatropine, scopolamine, tropicamide, eucatropine, and hydroxyamphetamine; sympathomimetics such as epinephrine; sedatives and hypnotics such as pentobarbital sodium, phenobarbital, secobarbital sodium, codeine, (a-bromoisovaleryl) urea, carbromal; psychic energizers such as 3-(2-aminopropyl) indole acetate and 3-(2-aminobutyl) indole acetate; tranquilizers such as reserpine, chlorpromayline, and thiopropazate; androgenic steroids such as methyl-testosterone and fluorymesterone; estrogens such as estrone, 17-β-estradiol, ethinyl estradiol, and diethyl stilbestrol; progestational agents such as progesterone, megestrol, melengestrol, chlormadinone, ethisterone, norethynodrel, 19-norprogesterone, norethindrone, medroxyprogesterone and 17-β-hydroxy-progesterone; humoral agents such as the prostaglandins, for example $PGE_1$, $PGE_2$ and $PGF_2$; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine, antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate; nutritional agents such as vitamins, natural and synthetic bioactive peptides and proteins, including growth factors, cell adhesion factors, cytokines, and biological response modifiers.

In one embodiment, the encapsulated material is a vaccine and the substance to be delivered is an antigen, such as vaccines such as smallpox, yellow fever, distemper, hog cholera, chicken pox, antivenom, scarlet fever, dyptheria toxoid, tetanus toxoid, pigeon pox, whooping cough, influenzae rabies, mumps, measles, poliomyelitic, and Newcastle disease. The antigen can be derived from a cell, bacteria, or virus particle, or portion thereof. As defined herein, antigen may be a protein, peptide, polysaccharide, glycoprotein, glycolipid, nucleic acid, or combination thereof, which elicits an immunogenic response in an animal, for example, a mammal, bird, or fish. The immunogenic response can be humoral or cell-mediated. In the event the material to which the immunogenic response is to be directed is poorly antigenic, it may be conjugated to a carrier, such as albumin, or to a hapten, using standard covalent binding techniques, for example, with one of the several commercially available reagent kits. Examples of preferred antigens include viral proteins such as influenza proteins, human immunodeficiency virus (HIV) proteins, and hepatitis A, B, or C proteins, and bacterial proteins, lipopolysaccharides such as gram negative bacterial cell walls and *Neisseria gonorrhea* proteins, and parvovirus.

Agents such as insecticides, pesticides, fungicides, rodenticides, plant nutrients, and growth promoters also can be encapsulated.

In a preferred embodiment, the active agent is a protein hormone or steroid, such as progesterone and estradiol. Other suitable proteins include nucleases, erythropoietin, human growth hormone, interferons, interleukins, tumor necrosis factor, adrenocorticotropic hormone, growth factors, colony-stimulating factors, and insulin.

The amount of active agent to be encapsulated and the amount used in the process will vary depending upon the particular active agent, the desired effect of the active agent at the planned release levels, and the time span over which the agent should be released.

The active agent can be dissolved or suspended directly in the polymer solution of the dispersed phase, or can be dispersed as droplets of a solution or emulsion in the polymer solution. The process can be used to encapsulate more than one active agent. The active agent also can be mixed with one or more excipients, such as stabilizing agents, known in the art.

II. Microencapsulation Processes

The microencapsulation processes described herein include (1) formation of an emulsion having (i) a dispersed phase, preferably containing an active agent, in a solution of polymer and solvent for the polymer, and (ii) a continuous phase containing a surfactant and a second solvent that is totally or partially immiscible with the first solvent; and (2) removal of the solvent for the polymer from the dispersed phase microdroplets to harden them, producing microparticles. The continuous phase optionally includes a quantity of dispersed phase solvent which reduces or eliminates partitioning of the solvent from the dispersed phase into the continuous phase during emulsification.

A. Processes for Making The Emulsion

In a preferred embodiment, the microencapsulation process includes the following general emulsion formation steps:

(1) Preparing a dispersed phase by dissolving an excipient (e.g., a polymer) in a solvent or solvent mixture;

(2) Adding at least one active agent to the dispersed phase to form a solution, suspension, or emulsion of active/excipient/solvent;

(3) Preparing a continuous phase by dissolving a suitable surfactant, protective colloid, or both, in a solvent that is totally or partially immiscible with the solvent in the dispersed phase, and optionally saturating, completely or incompletely, the continuous phase with the solvent for the dispersed phase;

(4) Combining the dispersed phase with the continuous phase under mixing conditions to form an emulsion, for example, by flowing the two phases continuously through a static mixer.

Formation of the emulsion can be done continuously, batchwise, or by a combination thereof.

1. Mixing

The dispersed (first) phase and the continuous (second) phase essentially can be mixed using any means capable of forming an emulsion having the desired dispersed phase droplet size. Suitable means include using static mixers (Maa, et al., *J. Microencapsulation* 13(4):419–33 (1996)), as well as dynamic mixing means such as agitators, homogenizers, sonication, and other process equipment known in the art.

Alternative means for mixing are provided herein. In one embodiment, the mixing is performed by pumping together the phases to be mixed through a length of pipe or tubing at conditions sufficient to create adequate mixing, i.e. enough turbulence to induce or enhance emulsion formation. Typically, Reynolds numbers necessary for this type of mixing are above the transition range. This generally refers to Reynolds numbers above 4000 (based on tube diameter).

Other static devices, such as restriction plates (flow constrictors) and filters, also can be used to create the required turbulence. In a preferred embodiment, nonstatic mixers are used as the mixing means. As used herein, the term "nonstatic mixer" refers to a device having elements that freely move within a flowing stream of the fluids to be mixed. Examples of nonstatic mixers include non-motorized turbines and certain flow indicators, such as a ball indicator. Another example is a flow though mixer head available on a Silverson homogenizer.

2. Continuous Emulsion Formation Using a Contacting Tank With Recycle

This process utilizes a recycle loop to provide a means of controlling residence time of the emulsion in a continuous process to achieve complete emulsification of the dispersed and continuous phases, thereby providing for more reproducible microspheres. The method can provide definitive mean residence times of the dispersed phase droplets before extraction. Additionally, since the only critical process pump rate is the recycle pump rate, rather than both the organic and aqueous phase pump rates, the number of critical variables that must be strictly controlled is reduced.

In a preferred embodiment, the process utilizes low-intensity emulsification, using surfactant in an amount effective to lower the surface tension of the fluids to permit formation of an emulsion without high energy processing equipment, such as homogenizers. An example of a continuous microencapsulation process using a contact tank with recycle is described below with reference to FIG. 1:

(A) Preparing in the Organic Phase Feedstock Tank a typical dispersed phase containing excipient (e.g., polymer) and active agent to be encapsulated. The organic phase composition should be adjusted to give a solution, or suspension, having a viscosity low enough for low-intensity emulsification, preferably less than 100 cP, more preferably less than 10 cP. Viscosity is dependent on the type and relative concentrations of polymer, solvent, surfactant, and active agent selected.

(B) Preparing in the Aqueous Phase Feedstock Tank a typical continuous phase containing surfactant and solvent in concentrations as needed to form a stable emulsion with the organic phase. Enough surfactant should be used to permit low-intensity emulsification. Typically, the surfactant concentration should be above its critical micelle concentration.

(C) Preparing a typical extraction phase, for example, water containing buffers to limit active agent solubility.

(D) Establishing an extraction phase flowrate through the Extraction Phase Feedline.

(E) Establishing an aqueous phase flowrate in the process with the recycle valve closed. After a sufficient volume of aqueous phase is fed to the contacting tank, start the recycle pump.

(F) Establishing an organic phase flowrate to the Contacting Tank. Emulsification occurs in the recycle loop. Exact process conditions needed for emulsification would need to be established for each type of organic phase and aqueous phase. Turbulent flow conditions in the recycle loop probably will be required to produce an emulsion having small enough disperse phase droplets. Agitation in the contacting tank can also be used to emulsify the organic and aqueous phases. Relative contributions to emulsification of each operation, agitation and recycle loop, can be optimized by those of skill in the art.

(G) Opening the recycle valve after set volumes of organic and aqueous phases have been fed to the Contacting Tank, allowing the emulsion to proceed downstream to the emulsion injection port into the extraction phase. The flowrate of emulsion should be adjusted to match the combined feedrates of organic and aqueous phases, thereby achieving a steady-state condition in the contacting tank. The pumping rate of the recycle pump and the recycle ratio can be adjusted to produce the desired process conditions, such as satisfactory emulsification, adequate mean residue, and emulsion take-off rates equivalent to organic/aqueous feedrates.

(H) Continuing the steady-state operating conditions until the organic phase is used up. Keep the aqueous phase flowing to flush the organic phase from the contacting tank. Quench, collect, wash, dry, and package the formed microparticles as needed using standard techniques.

This continuous emulsification process using a contacting tank with recycle can be adapted for use with other solvent removal techniques, such as those described below.

B. Processes For Solvent Removal

After formation of the emulsion, dispersed phase solvent is removed using one or more of the following processes. A microencapsulation process including these solvent removal processes can provide improved process control and product quality over methods disclosed in the prior art, especially in continuous processes for making microparticles.

1. Extraction Followed by Evaporation

This process combines the solvent removal techniques of extraction and evaporation. First a portion of the solvent is removed by extraction, and then evaporation is used to remove substantially all of the remaining solvent from the microparticles.

In a preferred embodiment, the solvent removal process includes steps (5) and (6) described below, which follow steps (1)–(4) described above:

(5) Adding the emulsion from step (4) to a suitable quantity of extraction phase to concentrate the dispersed phase or to induce skin formation at the interface between the dispersed phase and continuous phase to form microspheres, preferably by injecting the emulsion into a flowing stream of the extraction phase, wherein the extraction phase is
 (i) a non-solvent for the excipient;
 (ii) a solvent for the continuous phase components; and
 (iii) a limited solvent for the dispersed phase solvent, wherein the dispersed phase solvent has a solubility of 0.1% to 25% by weight in the extraction phase; and (6) Further removing dispersed phase solvent from the microspheres using an evaporative process, preferably while the microspheres remain in the extraction phase.

The formed microspheres then can be collected, washed, dried, and packaged using techniques known in the art. The process also can include using separation, or sizing, techniques known in the art for classifying microparticles by size.

The purpose of performing extraction and evaporation sequentially is twofold. First, the process can control the rate of solvent removal from the dispersed phase droplets in such a manner that the surface and internal structure of the resulting microspheres provides the desired release properties. Second, the process can provide the desired microsphere properties while minimizing the amount of extraction phase needed and therefore the cost of the total process. In both stages of solvent removal, extraction and evaporation, solvent must partition from the dispersed phase droplet into the surrounding medium. The rate of partitioning is proportional to the concentration gradient of the dispersed phase solvent across the interface that exists between the dispersed phase and extraction phase solvent, and can therefore be controlled by controlling the concentration of the dispersed phase solvent in the extraction phase throughout the process. This can be controlled by adjusting the total volume of extraction phase, either initially as described in U.S. Pat. No. 5,407,609 to Tice et al. or by further addition of extraction phase as described, for example, in Li et al.

Control of the solvent removal rate also can be achieved by evaporating solvent from the extraction phase at a rate that is matched to the desired rate of solvent removal during the latter stage of the encapsulation process. In general, a slow rate of solvent removal will produce microspheres having a dense internal structure, while a fast rate of solvent removal will produce microspheres having a porous internal structure. The relationship between internal structure and the rate of solvent removal depend on factors such as the physicochemical properties of the active agent, the excipient (composition and molecular weight), the dispersed phase solvent or solvents, the concentration of active agent and excipient in the dispersed phase.

The object of the extraction step is to effect an initial rapid reduction in solvent in the dispersed phase to establish the desired skin and internal structure. Once the desired extent and rate of extraction needed for a particular formulation have been determined, the minimum amount of extraction phase needed to achieve the desired extent of extraction within the desired extraction time frame and under a given set of conditions can be determined empirically or calculated using mathematical models, such as those described in Li et al. The object of the evaporation step is to maintain a relatively high driving force for partitioning of dispersed phase solvent, thereby minimizing the overall process time. The rate of evaporation needed to accomplish this objective can be determined by empirical methods or through the use of mathematical models.

Preferably between about 10% and about 90%, and more preferably between about 20% and 70%, of the solvent is removed by extraction.

The emulsification and solvent removal steps preferably are conducted in a continuous process. However, the solvent removal process can be practiced batchwise, continuously, or by a hybrid of the two, such as where the extraction step is continuous and the evaporation step is batchwise.

The evaporation step can be performed using techniques known in the art, such as described in U.S. Pat. No. 4,384,975 to Fong. Evaporation can be performed under atmospheric or reduced pressure conditions, and at ambient temperatures, or higher temperatures that do not harm the active agent or reduce its biological effectiveness. An example of a continuous evaporation process is one in which the process stream exiting the extraction step is passed through a falling-film or wiped-film evaporator.

2. Continuous Evaporation Process

In another preferred embodiment, the solvent is removed using only evaporation in a continuous process following a continuous emulsification process. No extraction is required, and consequently less process streams and process equipment are required than those including extraction.

In this process, the dispersed phase (DP) and continuous phase (CP) are prepared identically to the methods described above. It is preferred, however, that the CP:DP ratio be greater to provide for more dispersion during the subsequent evaporation process. Preferably, the CP:DP ratio is between 2 and 20, and more preferably between about 3 and 10. Following emulsification, the emulsion is transferred directly to an evaporative process. In a preferred embodiment, the emulsion flows into a large tank that is maintained under vacuum or reduced pressure, drawing off the solvent vapor. The tank may be heated, for example using an internal steam coil or external jacketing, in order to increase the rate of evaporation. The pressure and/or temperature selected depends on the solvent, polymer, and active agent selected, as well as the relative amounts of these materials.

3. Solvent Extraction By Membrane Separation

In a preferred embodiment of the microencapsulation process, steps (1) to (5) described above are employed and followed by a membrane separation step to remove the remainder of the solvent after the skin-forming extraction step, replacing the evaporation step (6). For example, a semipermeable membrane selective for the dispersed phase solvent, an ultrafiltration membrane with an appropriate molecular weight cut-off, or a microfiltration membrane of suitable pore size can be used in place of a portion of pipe downstream from the point of injection of the extraction phase, i.e. the extraction lag tube.

The rate of solvent removal is controlled by the properties of the membrane and the capacity of the fluid phase to hold the solvent. This solvent removal process preferably is performed on a continuous basis. The membrane separation process also provides fine control over the rate of solvent extraction, enabling one of skill in the art to create a microencapsulation process having a precise extraction profile, which, for example, can be computer controlled and adjusted during continuous operation, for instance, by adjusting the flow rate of the surrounding extraction fluid.

For example, in a product including microspheres between 25 and 125 $\mu$m in diameter, a microfiltration membrane having a pore size of 0.65 $\mu$m can be used. In a product including microspheres less than 10 $\mu$m in diameter, an ultrafiltration membrane with a molecular weight cut-off of 100,000 can be used as long as low or intermediate viscosity grades of poly(vinyl alcohol) are used as the process surfactant.

4. Incremental Extraction

Figure 5:
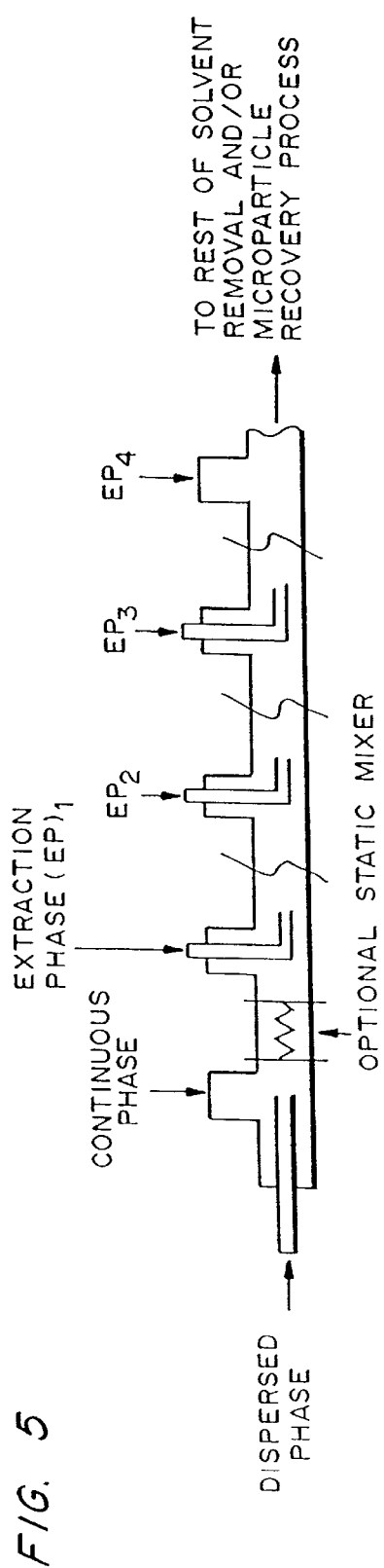
FIG. 5 is a process flow diagram of a preferred embodiment of the method for making microparticles using incremental extraction.

This solvent removal process includes incremental extraction, which involves introducing the extraction phase into the emulsion through multiple feed streams rather than a single feed stream. The extraction phase is thereby combined with the emulsion at two or more locations along the extraction lag tube rather than in one location, preferably in a continuous process. An example of this process is illustrated in FIG. 5. The incremental addition of the extraction phase should slow the extraction process, extending the amount of time provided to allow the microparticle to harden. To accomplish this goal, the amount of extraction phase (EP) introduced initially (e.g., in the first EP inlet) preferably is less than about 1.5 times the amount needed to induce skin formation in the dispersed phase droplet, which can be determined empirically or using available mathematical models.

Each incremental addition of extraction phase can be equal in its capacity to hold dispersed phase solvent, or the increments can differ. Furthermore, the position along the extraction lag tube at which the incremental additions are made can be controlled so that the extraction profile can be carefully programmed. With a sufficient number of extraction phase inlets, the extraction process effectively becomes a continuous process in which the rate of extraction is determined by the rate of addition of extraction phase, i.e. dilution of the emulsion.

The benefits of this process are twofold. First, when extraction is slowed relative to the "all at once" extraction processes of the prior art, a more homogeneous, dense microparticle is produced. Second, by slowing the initial extraction step, the skin can be minimized, thereby decreasing the resistance for solvent removal and making solvent removal more complete. The process also provides fine control over the extraction process, enabling one of skill in the art to create a microencapsulation process having a precise extraction profile, which, for example, can be computer controlled and adjusted during continuous operation.

The incremental extraction can be used to remove all the solvent to be removed from the microparticle, or a partial extraction process can be followed by an evaporation step to remove the solvent remaining after incremental extraction. The desired extent of extraction within the desired extraction time frame for a given set of conditions can be determined empirically or calculated using mathematical models, such as those described in Li et al.

5. Solvent Extraction Using Two Phases

This solvent extraction process uses only two phases, rather than the typical three phases. The same phase is used both to form the emulsion and to extract the solvent. Preferably that phase is aqueous.

This process requires less process equipment than a three phase continuous process for microencapsulation, since there is no need for an extraction phase tank, feed pump, feed line, or inlet port. While inherently simpler, the process requires careful control of the process variables, since there generally is only a narrow operating window at which the emulsion is stable enough to form spherical disperse phase droplets before extraction precipitates the polymer.

There are two primary process conditions that can be used in this process. The first condition is to operate at saturation levels of solvent, producing a solvent evaporation condition, rather than solvent extraction. The solvent is removed from a quench tank, possibly using a vacuum assist. Extraction times for this process condition, however, would be long. The second condition is to operate at below solvent saturation levels, producing a solvent extraction condition. Process variables for this condition, however, must be carefully adjusted to provide a metastable emulsion, in order to form dispersed phase droplets having desired diameters and surface characteristics.

As used herein, a metastable emulsion has transient stability for a long enough duration to allow the dispersed phase droplets to form and equilibrate to a given droplet size, that is, the emulsion is stable enough to fully develop before solvent extraction causes the polymer to begin precipitation. If the emulsion is not stable for a long enough time, the solvent will extract before the droplets form and the polymer will precipitate in strings or globs, rather than well defined droplets.

Figure 2:
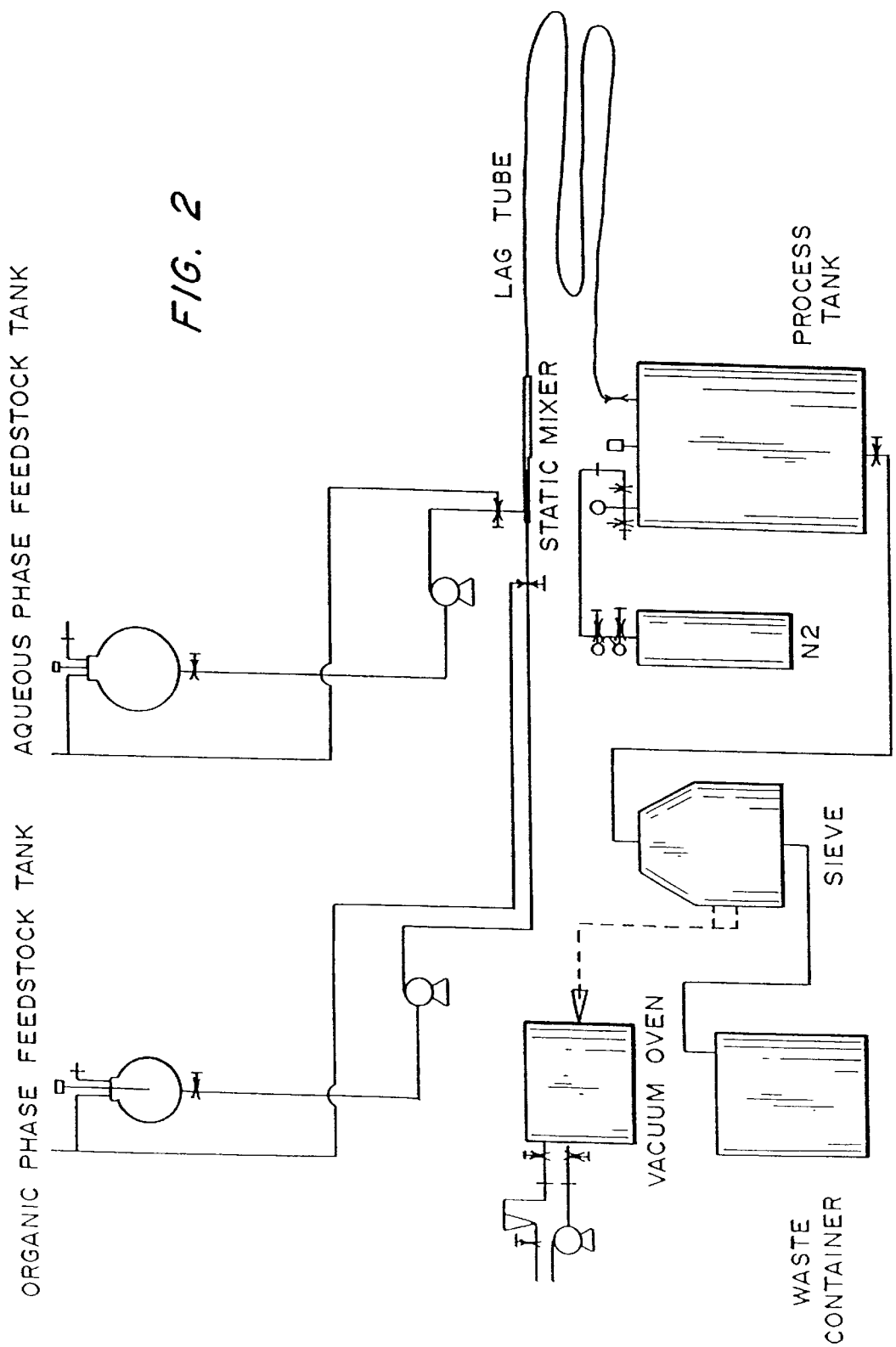
FIG. 2 is a process flow diagram of another embodiment of the method for making microparticles using a two phase continuous process.

In a preferred embodiment, the process utilizes low-intensity emulsification. An example of a continuous microencapsulation process using the two phase solvent extraction method is described below with reference to FIG. 2:

(A) Preparing in the Organic Phase Feedstock Tank a typical dispersed phase containing polymer and active agent to be microencapsulated. The organic phase composition should be adjusted to give a solution or suspension having a viscosity low enough for low-intensity emulsification. The viscosity is preferably less than 100 cP, more preferably less than 10 cP, and varies with the types and relative amounts of dispersed phase components selected.

(B) Preparing in the Aqueous Phase Feedstock Tank an aqueous phase. The aqueous phase should contain surfactant and solvent in concentrations needed to form a metastable emulsion with the organic phase. Enough solvent must be present in the extraction phase to prevent premature extraction of the solvent from the organic phase for the short time required to form spherical organic phase droplets of the selected diameter. For some processes and specific compounds, no additional solvent may be required. Surfactant should be present in concentrations above its critical micelle concentration.

(C) Establishing an aqueous phase flowrate to the static mixer.

(D) Establishing an organic phase flowrate to the static mixer. Continue operating until the organic phase is depleted, and then continue the aqueous phase flowing to flush the static mixer.

(E) Adding water to the Process Tank to increase the ratio of aqueous phase to organic phase in the tank to facilitate extraction of the solvent from the forming microparticles. The amount of water added is dependent primarily on the specific compounds used in a given process. However, enough water must be added to cause the formation of microspheres suitable for downstream processing. Quench, collect, wash, dry, and package, the formed microparticles as needed using known techniques.

6. Cryogenic Extraction

Solvent removal can be performed entirely or partially using a cryogenic extraction step. As used herein, the term "cryogenic extraction" refers to a process in which a cold extraction medium is used to freeze the polymer, the solvent for the polymer, or both in the emulsion.

As an emulsion droplet converts to a microsphere when the system components are in a fluid state, the processes of water entering the droplet, solvent leaving the droplet, polymer chains and active agent precipitating, and solid active agent becoming surrounded by different species all can be occur simultaneously, rendering the hardening process complicated and difficult to control. Cryogenic extraction, however, advantageously slows (or temporarily stops) many of these molecular processes so that they can be more easily controlled, that is, the hardening process does not have to be engineered to occur immediately or rapidly to keep emulsified droplets or solvent-wet microspheres from adhering to one another. The cryogenic process also provides an enhanced ability to control the mobility of the active agent, keeping it in the microsphere based on the appropriate selection of solvent and temperatures. The lower temperatures also can stabilize the active agent, particularly proteins.

In a preferred embodiment, an emulsion (dispersed phase in continuous phase) is formed and immediately chilled to freeze the DP. The CP is not frozen, rather the microspheres are isolated from the liquid following extraction of the DP solvent.

Selection of appropriate processing parameters for the cryogenic extraction step depends on several factors, including the choice of polymer, solvent for the polymer, and active agent. For example, the freezing point of the polymer and/or solvent is important to the selection of the extraction medium, as is the solubility of the solvent in the extraction medium at the lower temperature.

In a preferred embodiment, a solution of polymer and active agent is prepared in glacial acetic acid. Then the solution is emulsified in hexane near ambient temperatures and immediately transferred to cold mineral oil (e.g., −60° C.) to freeze the polymer and acetic acid. Next, the polymer/acetic acid/mineral oil mixture is slowly heated at a controlled rate such that the acetic acid partitions into the hexane at a temperature low enough that the polymer remains below its glass transition temperature throughout the solvent removal process.

In another preferred embodiment, a polymer/active agent mixture is prepared in ethyl lactate and emulsified in mineral oil at ambient temperatures. Then the emulsion is rapidly cooled by addition of a large excess of cold mineral oil (e.g., −80° C.). Next the mixture is slowly heated at a controlled rate to effect partitioning of the ethyl lactate into the mineral oil.

The cryogenic extraction step can be included in both batch and continuous processes for making microparticles. The cryogenic extraction step can be used as the sole means of solvent removal, or it can be used to remove a first portion of the solvent and followed by a second solvent removal step using conventional extraction and/or solvent evaporation.

The present invention will be further understood with reference to the following non-limiting examples.

EXAMPLE 1
Preparation of Fluoroscein Loaded Microspheres

Fluoroscein loaded microspheres were prepared using poly(DL-lactide) ("DL-PL"), having an inherent viscosity of 2.39 dL/g in $CHCl_3$ at 30° C. as the excipient. The dispersed phase (DP) consisted of a solution containing 10.03 g DL-PL and 0.1020 g of fluoroscein dissolved in 166.67 g of dichloromethane ("DCM"). The continuous phase (CP) was prepared by dissolving 5.26 g of dichloromethane in a 6 wt % solution of poly(vinyl alcohol) ("PVOH"), which was prepared by dissolving 21 g of AIRVOL™ 205 in 329 g of deionized water. The extraction phase (EP), which consisted of deionized water, was calculated to provide 90% extraction of the dichloromethane from the microspheres, as described below.

| | |
|---|---|
| Total DCM | = 166.67 g (DP) + 5.26 g (CP) |
| | = 171.93 g |
| Water required for 90% extraction | = (171.93 g)(0.9)/(0.016 g DCM/g $H_2O$) |
| | = 9,671.06 g |
| Extraction phase required | = water required − water in CP |
| | = 9,671.06 g − 329 g |
| | = 9342.9 g |

The required (90%) extraction phase, 9342.9 g of deionized water, was transferred to a 12 L spherical reaction flask fitted with a lid, a vacuum adapter connected a water aspirator, and an overhead stirrer fitted with a 6-blade TEFLON™ impeller. The stirrer on the EP was set to approximately 510 rpm.

The CP was transferred to a 1 L cylindrical reaction flask fitted with a lid and an overhead stirrer fitted with a 6-blade TEFLON™ impeller. The stirrer on the CP was set to approximately 650 rpm.

The DP was added to the CP with stirring to form the primary emulsion. After five minutes, the emulsion was transferred to the 12 L reaction flask containing the EP to initiate extraction of the DCM, thereby forming microspheres. After about ten minutes, the flask was closed and evacuated via the water aspirator. The pressure gradually was reduced from about 35 mm Hg below atmospheric to about 584 mm Hg below atmospheric over the next six hours.

After about 24 hr., the microspheres were collected on a fritted glass funnel, washed with deionized water, and vacuum dried to yield a free-flowing powder consisting of microspheres, the majority of which have a diameter between about 10 and 150 μm.

EXAMPLE 2
Preparation of Coumarin-6 Loaded Microspheres

Coumarin-6 loaded microspheres were prepared using poly(DL-lactide) ("DL-PL") having an inherent viscosity of 2.39 dL/g in $CHCl_3$ at 30° C. as the excipient. The dispersed-phase (DP) consisted of a solution containing 10.5 g DL-PL and 0.1173 g of Coumarin-6 dissolved in 168.0 g of dichloromethane ("DCM"). The continuous-phase (CP) was prepared by dissolving 5.49 g of dichloromethane in a 2 wt % solution of poly(vinyl alcohol) ("PVOH") which was prepared by dissolving 7 g of AIRVOL™ 205 in 343 g of deionized water. The extraction phase (EP), which consisted of 9758.8 g of deionized water, was calculated to provide 90% extraction of the dichloromethane from the microspheres, as described in Example 1.

The 9758.8 g of deionized water was transferred to a 12 L spherical reaction flask fitted with a lid, a vacuum adaptor connected to a water aspirator, and an overhead stirrer fitted with a 6-blade TEFLON™ impeller. The stirrer on the EP was set to approximately 510 rpm.

The CP was transferred to a 1 L cylindrical reaction flask fitted with a lid and an overhead stirrer fitted with a 6-blade TEFLON™ impeller. The stirrer on the CP was set to approximately 130 rpm.

The DP was added to the CP with stirring to form the primary emulsion. After four minutes, the emulsion was transferred to the 12 L reaction flask containing the EP to initiate extraction of the DCM, thereby forming microspheres. After about ten minutes, the flask was closed and evacuated via the water aspirator. The pressure gradually was reduced from about 25 mm Hg below atmospheric pressure to about 570 mm Hg below atmospheric pressure over the next 22 hr. After about 28 hrs., the microspheres were collected on a fritted glass funnel, washed with deionized water, and vacuum dried to yield a free-flowing powder consisting of microspheres, which were sieved to yield the size distributions shown in Table 1.

TABLE 1

Microsphere Size Range and Yield

| Size (μm) | Yield (wt %) |
|---|---|
| >500 | 3.9 |
| 425–500 | 10.0 |
| 355–425 | 29.0 |
| 300–355 | 20.7 |
| 250–300 | 18.2 |
| 212–250 | 10.1 |
| 150–212 | 8.1 |

Figure 3:
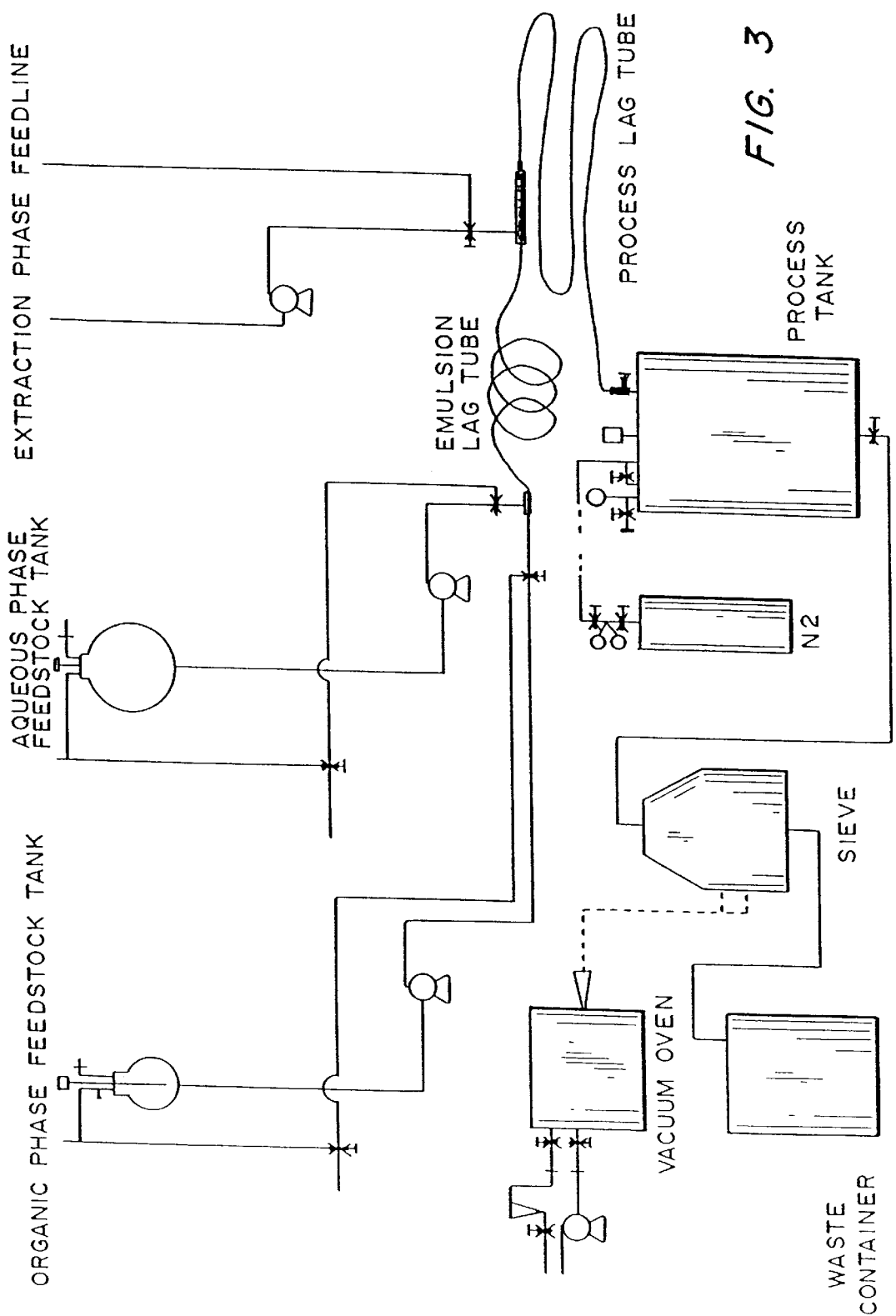
FIG. 3 is a process flow diagram of one embodiment of the method for making progesterone-loaded microspheres using direct injection of the extraction phase into the emulsion lag tube, in a continuous process.

EXAMPLE 3
Continuous Process for Making Microparticles Using Emulsification Induced by Lag Tube Turbulence Fifty percent by weight progesterone-loaded microspheres were produced using the process configuration shown in FIG. 3. The emulsion lag tube was constructed from 12 ft. (366 cm) of ⅛" (3.175 mm) polytetrafluoroethylene (TEFLON™) tubing having a wall thickness of 0.030" (0.762 mm). The tubing was selected to provide turbulent flow corresponding to a Reynolds number of approximately 4100 at an emulsion flow rate of 1240 cm/s. The procedure was as follows.

Figure 4:
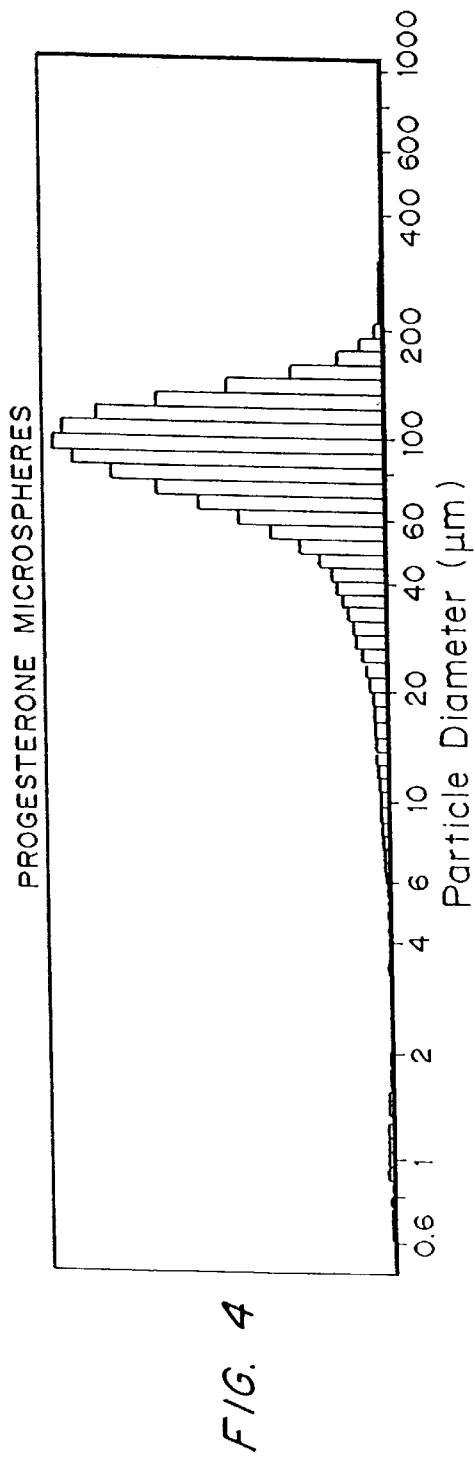
FIG. 4 is a graph showing microparticle size distribution for microparticles using one embodiment of the method described herein.

1. An organic (dispersed) phase was prepared by dissolving about 100 g of progesterone and 100 g of 65:35 poly(dl-lactide-co-glycolide), I.V.=0.65 dL/g in 1600 g of DCM. The organic phase viscosity was about 8 cP.
2. An aqueous (continuous) phase consisting of a solution of 0.7 wt.% polyvinyl alcohol containing 1.4 wt.% DCM was prepared by dissolving 70 g of polyvinyl alcohol, 85–89% hydrolyzed and 32–36 cP of a 4% aqueous solution, in 10 kg of deionized water using standard techniques, and then adding 140 g of DCM to the solution. The surface tension was allowed to equilibrate, producing an aqueous phase with a viscosity of about 2 cP.
3. An extraction phase, consisting of deionized water, was prepared.
4. An extraction phase flowrate of 3 L/min. was established.
5. An aqueous phase flowrate of between about 240 and 900 mL/min. was established with the recycle valve closed. This flowrate was varied to assess the effects of flowrate on emulsification.
6. An organic phase flowrate of 70 mL/min. was established with the recycle valve closed.
7. At the start of the production run, the aqueous phase recycle valve was turned to the open (run) position, and the aqueous phase allowed to fill the emulsion lag tube. Then, the organic phase recycle valve was turned to the open (run) position, mixing the phases and forming the emulsion in the emulsion lag tube.
8. Near the outlet of the emulsion lag tube, the extraction phase was introduced. Extraction was completed in a continuous manner in the process lag tube and process tank.
9. The microspheres were produced, collected, washed, and dried. FIG. 4 shows a graph of the particle size distribution of the resulting progesterone-loaded microspheres.

Modifications and variations of the present invention will be obvious to those skilled in the art from the foregoing detailed description. Such modifications and variations are intended to come within the scope of the appended claims.

We claim:

1. A method for making microparticles, the method comprising
   (a) preparing a first phase comprising a solution of an excipient dissolved in a first solvent;
   (b) preparing a second phase comprising
      (i) a second solvent which is totally or partially immiscible in the first solvent, and
      (ii) a surfactant;
   (c) preparing an extraction phase comprising a third solvent which is a nonsolvent for the excipient, a solvent for the second phase, and a solvent for the first solvent, wherein the first solvent has a solubility in the extraction phase of between about 0.1% and 25% by weight;
   (d) mixing the first phase and the second phase to form an emulsion having microdroplets comprising the first phase;
   (e) mixing a portion of the extraction phase in the emulsion in an amount sufficient to initiate hardening of the microdroplets, thereby forming microparticles; and
   (f) evaporating from the microparticles substantially all of the solvent remaining in the microparticles following step (e).

2. The method of claim 1 wherein the excipient is a polymer.

3. The method of claim 2 wherein the polymer is selected from the group consisting of polyhydroxyacids, polyanhydrides, polyorthoesters, polyetheresters, polycaprolactone, polyesteramides, cellulose ethers, cellulose esters, polyacrylates, polyurethanes, polystyrenes, polyvinyl chloride, polyvinyl fluoride, poly(vinyl imidazole), chlorosulphonate polyolefins, polyethylene oxide, copolymers thereof, and blends thereof.

4. The method of claim 2 wherein the polymer is selected from the group consisting of poly(lactide)s, poly(glycolide)s, poly(lactide-co-glycolide)s, poly(lactic acid)s, poly(glycolic acid)s, poly(lactic acid-co-glycolic acid)s, polyanhydrides, polyorthoesters, polyetheresters, polycaprolactone, polyesteramides, cellulose ethers, cellulose esters, acrylics, and blends thereof.

5. The method of claim 1 further comprising dissolving or dispersing an active agent in the first phase of step (a).

6. The method of claim 5 wherein the active agent is selected from the group consisting of peptides and proteins, sugars and polysaccharides, nucleic acid molecules, drugs, and imaging agents.

7. The method of claim 6 wherein the active agent is a protein selected from the group consisting of nucleases, erythropoietin, interferons, interleukins, tumor necrosis factor, adrenocorticotropic hormone, growth factors, colony-stimulating factors, and insulin.

8. The method of claim 5 wherein the active agent is selected from the group consisting of antibiotics, steroids, decongestants, neuroactive agents, anesthetics, and sedatives.

9. The method of claim 5 wherein the active agent is an antigen in an amount effective for use as a vaccine.

10. The method of claim 1 wherein the second phase of step (b) further comprises first solvent.

11. The method of claim 10 wherein the first solvent in the second phase of step (b) is in an amount sufficient to saturate the second phase.

12. The method of claim 1 wherein the first solvent is selected from the group consisting of ethyl acetate, dichloromethane, ethyl formate, water, acetone, chloroform, methanol, ethanol, and miscible blends thereof.

13. A method for making microparticles, the method comprising
   (a) preparing a first phase comprising a solution of an excipient dissolved in a first solvent;
   (b) preparing a second phase comprising
      (i) a second solvent which is totally or partially immiscible in the first solvent, and
      (ii) a surfactant;
   (c) preparing an extraction phase;
   (d) mixing the first phase and the second phase to form an emulsion having microdroplets comprising the first phase;
   (e) combining the emulsion with the extraction phase at a temperature to freeze the excipient in the microdroplets, thereby forming microparticles; and
   (f) extracting at least a portion of the first solvent from the microparticles.

14. The method of claim 13 wherein the extraction phase of step (c) is selected from the group consisting of mineral oils and glycerol.

15. The method of claim 13 wherein the extraction phase of step (c) comprises the second solvent.

16. The method of claim 13 wherein the second phase of step (b) further comprises first solvent.

17. The method of claim 16 wherein the first solvent in the second phase of step (b) is in an amount sufficient to saturate the second phase.

18. A method for making microparticles comprising
(a) preparing a first phase comprising a solution of an excipient dissolved in a first solvent;
(b) preparing a second phase comprising
  (i) a second solvent which is totally or partially immiscible in the first solvent, and
  (ii) a surfactant;
(c) preparing an extraction phase comprising a third solvent which is a nonsolvent for the excipient, a solvent for the second phase, and a solvent for the first solvent, wherein the first solvent has a solubility in the extraction phase of between about 0.1% and 25% by weight;
(d) mixing the first phase and the second phase to form an emulsion having microdroplets comprising the first phase; and
(e) sequentially introducing discrete increments of the extraction phase into the emulsion, wherein each increment of extraction phase extracts a portion of the solvent from the microdroplets, thereby forming microparticles.

19. The method of claim 18 wherein the discrete increments are introduced into the emulsion through a plurality of feed streams in a continuous process.

20. The method of claim 18 wherein the second phase of step (b) further comprises first solvent.

21. The method of claim 20 wherein the first solvent in the second phase of step (b) is in an amount sufficient to saturate the second phase.

22. A method for making microparticles comprising
(a) preparing a first phase comprising a solution of an excipient dissolved in a first solvent;
(b) preparing a second phase comprising
  (i) a second solvent which is totally or partially immiscible in the first solvent, and
  (ii) a surfactant;
(c) preparing an extraction phase comprising a third solvent which is a nonsolvent for the excipient, a solvent for the second phase, and a solvent for the first solvent;
(d) flowing the first phase and the second phase into a contacting vessel having a pumped recycle loop to form an emulsion having microdroplets comprising the first phase; and
(e) mixing the emulsion and the extraction phase to remove solvent from the microdroplets, thereby forming microparticles.

23. The method of claim 22 wherein the solvent removal in step (e) is conducting using a technique selected from the group consisting of extraction, evaporation, membrane separation, and combinations thereof.

24. The method of claim 22 wherein the second phase of step (b) further comprises first solvent.

25. The method of claim 24 wherein the first solvent in the second phase of step (b) is in an amount sufficient to saturate the second phase.

26. The method for making microparticles, the method comprising
(a) preparing a first phase comprising a solution of an excipient dissolved in a first solvent;
(b) preparing a second phase comprising
  (i) a second solvent which is totally or partially immiscible in the first solvent, and
  (ii) a surfactant in an amount producing a concentration of surfactant greater than the critical micelle concentration;
(c) mixing the first phase and the second phase to form a metastable emulsion; and
(d) adding second solvent to the emulsion to extract at least a portion of the first solvent, thereby forming microparticles.

27. The method of claim 26 wherein the viscosity of the first phase is less than about 100 cP and the second phase is aqueous.

28. The method of claim 27 wherein the viscosity of the first phase is less than about 10 cP.

29. The method of claim 26 wherein the second phase of step (b) further comprises first solvent.

30. The method of claim 29 wherein the first solvent in the second phase of step (b) is in an amount sufficient to saturate the second phase.

31. A method for making microparticles comprising
(a) preparing a first phase comprising a solution of an excipient dissolved in a first solvent;
(b) preparing a second phase comprising
  (i) a second solvent which is totally or partially immiscible in the first solvent, and
  (ii) a surfactant;
(c) preparing an extraction phase comprising a third solvent which is a nonsolvent for the excipient, a solvent for the second phase, and a solvent for the first solvent;
(d) mixing the first phase and the second phase to form an emulsion having microdroplets comprising the first phase;
(e) mixing a portion of the extraction phase with the emulsion in an amount sufficient to initiate hardening of the microdroplets, thereby forming microparticles, and
(f) using a membrane separation technique to remove from the microparticles substantially all of the solvent remaining in the microparticles.

32. The method of claim 31 wherein the second phase of step (b) further comprises first solvent.

33. The method of claim 32 wherein the first solvent in the second phase of step (b) is in an amount sufficient to saturate the second phase.

34. A method of making microparticles, the method comprising
(a) preparing a first phase comprising a solution of an excipient dissolved in a first solvent;
(b) preparing a second phase comprising
  (i) a second solvent which is totally or partially immiscible in the first solvent, and
  (ii) a surfactant;
(c) mixing the first phase and the second phase to form an emulsion having microdroplets comprising the first phase and evaporating the first solvent from the emulsion in a continuous process, thereby forming microparticles.

35. The method of claim 1 wherein the step (e) is conducted using a technique selected from the group consisting of cryogenic extraction and incremental extraction.

36. A microparticle made by the method of claim 1.

* * * * *